United States Patent
Bornhop et al.

(10) Patent No.: US 6,381,025 B1
(45) Date of Patent: Apr. 30, 2002

(54) INTERFEROMETRIC DETECTION SYSTEM AND METHOD

(75) Inventors: Darryl J. Bornhop, Lubbock, TX (US); Kelly Swinney, Martinsville, VA (US); Dmitry Markov, Lubbock, TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 09/519,860

(22) Filed: Mar. 6, 2000

Related U.S. Application Data

(60) Provisional application No. 60/149,459, filed on Aug. 19, 1999.

(51) Int. Cl.[7] .............................................. G01N 21/41
(52) U.S. Cl. ...................................... 356/517; 356/134
(58) Field of Search ................................ 356/517, 361, 356/480, 134

(56) References Cited

U.S. PATENT DOCUMENTS

| | | | |
|---|---|---|---|
| 4,660,974 A | * 4/1987 | Mächler et al. | ............. 356/128 |
| 4,908,112 A | 3/1990 | Pace | |
| 4,950,074 A | 8/1990 | Fabricius et al. | |
| 5,073,024 A | * 12/1991 | Valette et al. | ................ 356/345 |
| 5,108,179 A | 4/1992 | Myers | |

(List continued on next page.)

OTHER PUBLICATIONS

Kelly Swinney et al., "Micro–interferometric Backscatter Detection Using a Laser Diode," Analytica Chimica Acta 400, 265–280 (1999).

Kelly Swinney et al., "Ion Analysis Using Capillary Electrophoresis with Refractive Index Detection," Microchemical Journal Journal 62, 154–163 (1999).

Yolanda Fintschenko et al., "Silicon Microtechnology and Microstructures in Separation Science," Journal of Chromatography A, 819, 3–12 (1998).

E. F. Schipper et al., "Waveguide Mach–Zender Interferometer as Atrazine Sensor," Analytical Chemistry 1998, 70, 1192–1197 (Mar. 15, 1998).

Yanzhuo Deng et al., "On–column Refractive–index Detection Based on Retroreflected Beam Interference for Capillary Electrophoresis," Applied Optics, vol. 37, No. 6, 998–1005 (Feb. 20, 1998).

Norbert Burggraf et al., "Holographic Refractive Index Detector for Application in Microchip–based Separation Systems," Analyst, vol. 123, 1443–1447 (Jul., 1998).

(List continued on next page.)

*Primary Examiner*—Robert Kim
*Assistant Examiner*—Phil Natividad
(74) *Attorney, Agent, or Firm*—Jones, Tullar & Cooper, PC

(57) ABSTRACT

An optical detection scheme for on-chip, high sensitivity refractive index detection is based on micro-interferometry, and allows for picoliter detection volumes and universal analyte sensitivity. The invention employs three main elements: a source of coherent light, such as a VCSEL, laser diode or He—Ne laser; an etched channel of capillary dimensions in a substrate for reception of a sample to be analyzed; and a photodetector for detecting laser light reflected off of the channel. The laser source generates an unfocused laser beam that is incident on the etched channel. A unique multi-pass optical configuration is inherently created by the channel characteristics, and is based on the interaction of the unfocused laser beam and the curved surface of the channel, that allows RI measurements in small volumes at high sensitivity. The entire device, including the laser and the photodetector can be formed on a single microchip. The detector has numerous applications, including universal/RI detection for CE (capillary electrophoresis), CEC (capillary electrochromatography) and FIA, physiometry, cell sorting/detection by scatter, ultra micro calorimetry, flow rate sensing and temperature sensing.

47 Claims, 4 Drawing Sheets

U.S. PATENT DOCUMENTS

| | | | |
|---|---|---|---|
| 5,120,131 A | * | 6/1992 | Lukosz ........................ 356/351 |
| 5,125,740 A | | 6/1992 | Sato et al. |
| 5,165,005 A | | 11/1992 | Klainer et al. |
| 5,173,747 A | | 12/1992 | Boiarski et al. |
| 5,215,883 A | | 6/1993 | Chu |
| 5,273,633 A | | 12/1993 | Wang |
| 5,305,071 A | | 4/1994 | Wyatt |
| 5,325,170 A | * | 6/1994 | Bornhop ..................... 356/128 |
| 5,377,008 A | * | 12/1994 | Ridgway et al. ............ 356/361 |
| 5,633,708 A | | 5/1997 | Svendsen |
| 5,636,017 A | * | 6/1997 | Bruno et al. ................. 356/246 |
| 5,663,790 A | | 9/1997 | Ekstrom et al. |
| 5,694,210 A | | 12/1997 | Newell et al. |
| 5,740,291 A | | 4/1998 | De Lasa et al. |
| 5,770,029 A | | 6/1998 | Nelson et al. |
| 5,815,258 A | | 9/1998 | Nakanishi |
| 5,824,204 A | | 10/1998 | Jerman |
| 5,841,914 A | | 11/1998 | Shieh et al. |
| 5,846,708 A | | 12/1998 | Hollis et al. |
| 5,852,495 A | | 12/1998 | Parce |
| 5,867,266 A | | 2/1999 | Craighead |

OTHER PUBLICATIONS

G. J. Veldhuis et al., "Highly–sensitive Passive Integrated Optical Spiral–Shaped Waveguide Refractometer," Applied Physics Letters, 71 (20), 2895–2897 (Nov. 17, 1997).

Christopher K. Kenmore, et al., "Refractive–index Detection by Interferometric Backscatter in Packed–capillary High–performance Liquid Chromatography," Journal of Chromatography A, 762, 219–225 (1997).

Darryl J. Bornhop et al., "Polarmetry in Capillary Dimensions," Analytical Chemistry, vol. 68, No. 10, 1677–1684 (May 15, 1996).

Darryl J. Bornhop et al., "Microvolume Index of Refraction Determinations by Interferometric Backscatter," Applied Optics, vol. 34, No. 18, 3234–3239 (Jun. 20, 1995).

* cited by examiner

INTERFEROMETRIC DETECTION SYSTEM AND METHOD

CROSS REFERENCE TO RELATED APPLICATIONS

The present application claims the benefit under 35 USC 119 (e), of U.S. Provisional Application No. 60/149,459, filed Aug. 19, 1999.

BACKGROUND OF THE INVENTION

1. Field of Invention

The present invention relates to an interferometric detection system and method that can be used, for example, for detection of refractive index changes in picoliter sized samples for chip-scale analyses. The detection system has numerous applications, including universal/RI detection for CE (capillary electrophoresis), CEC (capillary electrochromatography) and FIA, physiometry, cell sorting/detection by scatter, ultra micro calorimetry, flow rate sensing and temperature sensing.

2. Description of the Prior Art

Capillary-based analysis schemes, biochemical analysis, basic research in the biological sciences such as localized pH determinations in tissues and studies in protein folding, detection and study of microorganisms, and the miniaturization of instrumentation down to the size of a chip all require small volume detection. In fact miniaturization of fluid handling systems is at the heart of the genomics and proteomics technology effort. These systems allow one to manipulate single cells or even single macromolecules and it has been recently shown that when liquid handling systems are shrunk to the micron and sub-micron range, small Reynolds numbers and mixing nanoliters in microseconds are possible. Yet, detecting the absolute temperature changes produced in a nanoliter volume T-jump experiment has not been possible. Additionally, the ability to measure biological events such as cold denaturation and binding constants at low temperatures is critically important, but currently limited by existing instrumentation. The potential to perform cellular level investigations and to do high throughput analysis can potentially be realized by using a new generation of analytical instruments based on "chips", known as miniaturized total analysis systems ($\mu$-TAS). In fact, commercial "laboratory on a chip" devices are now available. It has long been known that the volumetric constraints imposed on the detection system used in $\mu$-TAS will dictate the utility of these techniques that are based on microfabrication. Typical injection volumes for $\mu$-TAS are in the nanoliter ($10^{-9}$L) to picoliter ($10^{-12}$L) range and ultimately impart severe constraints on the detection system. In short, the detection volume must be comparable to the injection volume while not sacrificing sensitivity. Yet, the development of $\mu$-TAS systems has been accompanied by the implementation, and to a much lesser extent, the improvement of "conventional" detection systems.

Most approaches for $\mu$-TAS or on-chip detection have been based on "conventional" optical measurements, primarily absorption, fluorescence or electrochemical. Unfortunately, absorbance measurements are limited in chip-scale techniques because of their inherent path length sensitivity and solute absorbtivity. The fact that the channel dimensions are normally 10–20 $\mu$m deep and 20–50 $\mu$m wide further exacerbates the S/N limitation for absorbance determinations ultimately limiting picoliter volume detection limits to the range of 0.1–0.01 mM.

With the advent of lasers, light sources possessing unique properties including high spatial coherence, monochromaticity and high photon flux, unparalleled sensitivity and selectivity in chemical analysis is possible. The advantages of using lasers in micro-chemical analysis are well known and have been demonstrated thoroughly. Over the past five years, technical advances in the laser have lead to reduced cost, enhanced reliability and availability of new wavelengths or multi-wavelength scanning systems. The result has been the demonstration of a number of high sensitivity/micro-volume detection methodologies for universal analysis. For example laser-induced fluorescence (LIF) can provide extremely low detection limits, with most laboratories able to detect as few as $10^5$ molecules. In fact, recent developments in ultra-high sensitivity LIF have allowed single molecule detection to be performed 'on-chip'. While fluorescence is an inherently sensitive detection method, it can be expensive to implement and is only applicable to solutes that are either, naturally fluorescent (the number of such molecules is actually quite small) or that can be chemically modified to fluoresce. Other approaches to on-chip detection have primarily included thermal conductivity, electroluminescence and electrochemical methods. However, these technologies are also expensive and hard to implement.

Refractive index detection is still a common technique used in chemical and biochemical analysis that has been successfully applied to several small volume analytical separation schemes. For various reasons, RI detection represents an attractive alternative to fluorescence and absorbance. First, RI detection is relatively simple. Second, it can be used with a wide range of buffer systems. Finally, RI detection is universal, theoretically allowing detection of any solute, making it particularly applicable to solutes with poor absorption or fluorescence properties. However, for a number of reasons, attempts toward implementation of RI detection in chip-scale analyses has been somewhat problematic.

Previous attempts for on-chip RI detection have generally involved the use of either waveguiding or interferometry. Among these techniques are the Mach-Zender approach, the porous silicon-based optical interferometer, surface plasmon resonance (SPR) (and related) techniques, the 'on-chip' spiral-shaped waveguide refractometer, and the holographic forward scatter interferometer. While each of the aforementioned RI measurement techniques can produce impressive results, they are all limited when applied to on-chip detection with chip scale analyses. In general, the path length dependency of evanescent wave-based techniques like SPR or the Mach Zender interferometer, demands a long sensing region be in contact with the separation fluid resulting in an optical "detection" volume too large to be compatible with chip-scale analyses.

The porous silicon-based optical interferometer (a Fabry-Perot system) can provide pico- and even femtomolar analyte sensitivity, but for the RI signal to be produced, this sensor requires (as do the SPR sensors) that the exogenous 'reporter' molecules be attached to the surface of the silicon and subsequently bind to the desired or target solute. This methodology of using molecular recognition which leads to an RI change can be used as an on-chip detector, provides solute selectively, leading inherently to high sensitivity, but is limited by reaction kinetics and the need to do sophisticated biochemistry and surface immobilization. These chemistries are normally diffusion limited and thus take time. In addition, solute events produced in CE, FIA or chip scale HPLC must be detected as they traverse the detector. Temporal constraints can be severe and range from 10's of milli-seconds to several minutes. Thus the peak must be sensed or analyzed in the probe volume during the elution time. Furthermore, technologies such as SPR do not provide the option to directly monitor μ-Vol. temperature changes as are needed to study, for example, reaction kinetics or to perform on-chip flow rate sensing.

The holographic forward scatter interferometer is thus far, the most promising approach for on-chip universal or RI detection in CE, and uses a holographic grating and a forward scattering optical configuration. However, while research on this technique has clearly shown the potential for doing on-chip RI sensing, the sensitivity of the forward scatter technique employed is inherently limited because it is has a single pass optical configuration, e.g. the probe beam traverses only once through the detection channel.

In view of the foregoing, a need still remains for an RI detection technique that is sensitive, universal can probe ultra-small volumes, is compatible with the chip-based format and can be employed for temperature and flow rate sensing of ultra-small volumes.

SUMMARY OF THE INVENTION

The present invention fulfills the need for a new sensing methodology applicable to μ-TAS through provision of an interferometric detection system and method that circumvent the drawbacks of 'standard' interferometric methods and the limitations of the forward scatter technique. The system includes a source of coherent light, such as a diode or He—Ne laser, a channel of capillary dimensions that is preferably etched in a substrate for reception of a sample to be analyzed, and a photodetector for detecting backscattered light from the sample at a detection zone.

The laser source generates an easy to align simple optical train comprised of an unfocused laser beam that is incident on the etched channel for generating the backscattered light. The backscattered light comprises interference fringe patterns that result from the reflective and refractive interaction of the incident laser beam with the channel walls and the sample. These fringe patterns include a plurality of light bands whose positions shift as the refractive index of the sample is varied, either through compositional changes or through temperature changes, for example. The photodetector detects the backscattered light and converts it into intensity signals that vary as the positions of the light bands in the fringe patterns shift, and can thus be employed to determine the refractive index (RI), or an RI related characteristic property, of the sample. A signal analyzer, such as a computer or an electrical circuit, is employed for this purpose to analyze the photodetector signals, and determine the characteristic property of the sample.

Preferably, the channel has a generally hemispherical cross sectional shape. A unique multi-pass optical configuration is inherently created by the channel characteristics, and is based on the interaction of the unfocused laser beam and the curved surface of the channel, that allows interferometric measurements in small volumes at high sensitivity. Additionally, if a laser diode is employed as the source, not only does this enable use of wavelength modulation for significant improvements in signal-to-noise ratio, but it also makes it possible to integrate the entire detector device directly onto a single microchip.

The detector can be employed for any application that requires interferometric measurements, however, the detector is particularly attractive for making universal solute quantification, temperature and flow rate measurements. In these applications, the detector provides ultra-high sensitivity due to the multi-pass optical configuration of the channel.

In the temperature measuring embodiment, the signal analyzer receives the signals generated by the photodetector and analyzes them using the principle that the refractive index of the sample varies proportionally to its temperature. In this manner, the signal analyzer can calculate temperature changes in the sample from positional shifts in the detected interference fringe patterns.

In the flow measuring embodiment, the same principle is also employed by the signal analyzer to identify a point in time at which a thermal perturbation is detected in a flow stream in the channel. First, a flow stream whose flow rate is to be determined, is locally heated at a point that is known distance along the channel from the detection zone. The signal analyzer for this embodiment includes a timing means or circuit that notes the time at which the flow stream heating occurs. Then, the signal analyzer determines from the positional shifts of the light bands in the interference fringe patterns, the time at which the thermal perturbation in the flow stream arrives at the detection zone. The signal analyzer then determines the flow rate from the time interval and distance values.

BRIEF DESCRIPTION OF THE DRAWINGS

The features and advantages of the present invention will become apparent from the following detailed description of a number of preferred embodiments thereof, taken in conjunction with the accompanying drawings, in which.

DETAILED DESCRIPTION OF THE PREFERRED EMBODIMENTS

Figure 1:
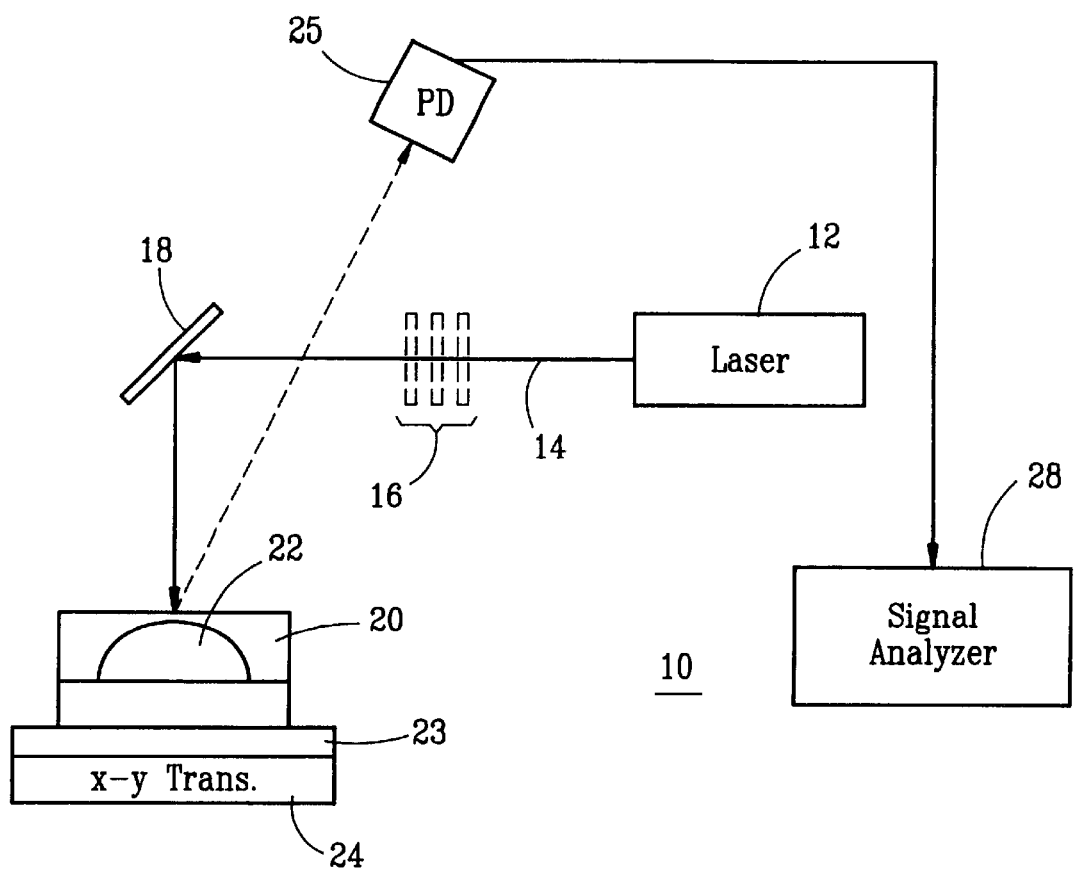
FIG. 1 is a schematic block diagram of an interferometric detection system that is constructed in accordance with a first preferred embodiment of the present invention.

With reference now to a first preferred embodiment of the present invention, an interferometric detection system 10 is illustrated in FIG. 1 which makes use of a technique that employs backscattered light to determine the RI or RI related characteristic properties of a sample. The backscatter detection technique is generally disclosed in U.S. Pat. No. 5,325,170 to Bornhop, which is hereby incorporated by reference. However, in the present invention where backscatter detection is used for "on-chip" detection with ultra-small sample volumes, the technique employed is referred to as Micro-Interferometric Backscatter Detection or MIBD.

The interferometric detection system 10 includes a laser or other source of coherent light 12, which is preferably a low power (3–15 mW) laser (He/Ne or Diode), and generates a laser beam 14. As with any interferometric technique for micro-chemical analysis, MIBD benefits from many of advantages lasers provide, including high spatial coherence, monochromaticity, and high photon flux. The intensity of the laser beam 14 can be reduced as needed with a series of optional neutral density filters 16 (e.g., optical density of 0.5, 1.0, 0.3 respectively). Upon reduction of the intensity, the beam 14 is directed to an optional mirror 18 that is angled at approximately 45° with respect to the plane of propagation of the laser beam 14. The mirror 18 re-directs the beam 14 onto a substrate chip 20 having a channel 22 formed therein, preferably by etching, for reception of a sample volume to be analyzed. It will be understood that the mirror 18 can be deleted, and the laser 12 can be repositioned to aim the laser beam 14 directly at the etched channel 22 if desired.

The chip 20 is preferably formed of silica, but can be any other suitable optically reflective material, such as plastic. The only requirement is that the material from which the chip 20 is made, must have a different index of refraction than that of a sample volume to be tested. In the exemplary embodiment of FIG. 1, the chip 20 is shown mounted on a peltier temperature controlled A1 support block 23, which in turn is affixed to an X-Y translation stage 24 that allows adjustment of the chip 20 relative to the laser beam 14. More particularly, the chip 20 is preferably tilted slightly (e.g., approximately 7°) so that the (nearly direct) backscattered light from the channel 22 can be directed onto a photodetector 25. The purpose of the temperature controlled support block 23 is to insure that the sample in the channel 22 is maintained at a constant temperature since the RI of a sample is known to vary linearly with its temperature. Alternatively, this characteristic also allows the detection system 10 to be utilized for making very accurate temperature measurements.

Figure 4:
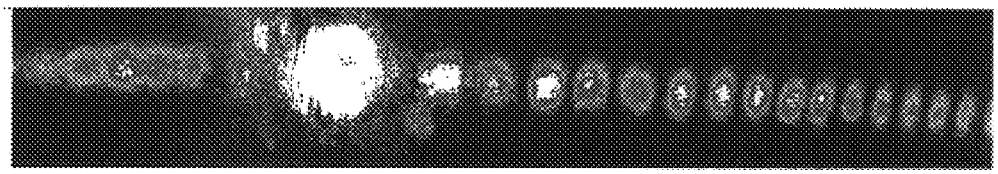
FIG. 4 is an illustration of an interference fringe pattern that is produced by the system of FIG. 1.

The photodetector 25 can be one of any number of image sensing devices, including a bi-cell position sensor, a CCD camera and laser beam analyzer (such as an LBA 100A, Spiricon, Inc. UT) assembly, a slit-photodetector assembly, an avalanche photodiode, or any other suitable photodetection device. The backscattered light comprises interference fringe patterns that result from the reflective and refractive interaction of the incident laser beam 14 with the walls of the channel 22 and the sample. These fringe patterns include a plurality of light bands (see FIG. 4) whose positions shift as the refractive index of the sample is varied, either through compositional changes or through temperature changes, for example. The photodetector 25 detects the backscattered light and converts it into one or more intensity signals that vary as the positions of the light bands in the fringe patterns shift. For fringe profiling, the photodetector 25 is preferably mounted above the chip 20 at an approximately 45° angle thereto.

The intensity signals from the photodetector 25 are fed into a signal analyzer 28 for fringe pattern analysis, and determination therefrom of the RI or an RI related characteristic property of a sample in the channel 22. The signal analyzer 28 can be a computer (e.g., a PC) or a dedicated electrical circuit, for example. Preferably, the signal analyzer 28 includes the programming or circuitry necessary to determine from the intensity signals, the RI or other characteristic properties of the sample to be determined, such as temperature or flow rate, for example.

Figure 2:
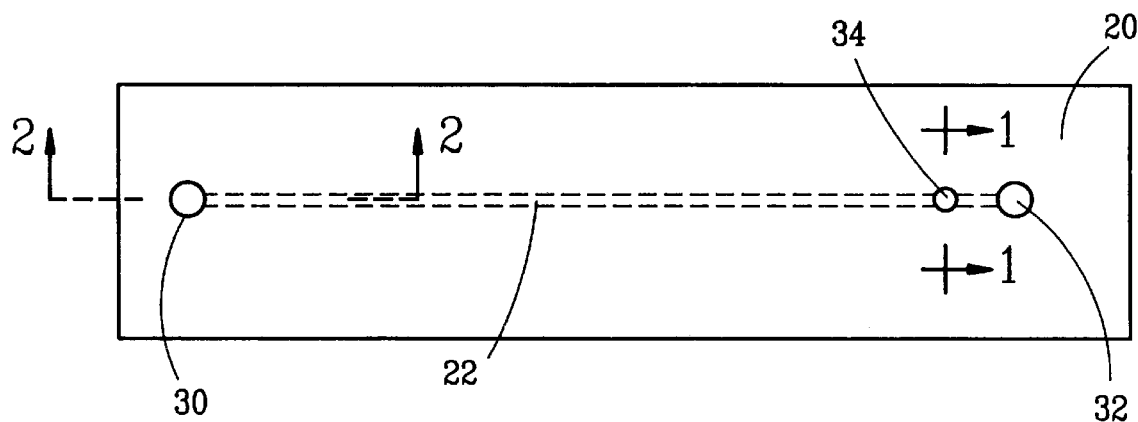
FIG. 2 is a diagrammatic illustration of a silica or other material chip having a channel therein that forms a part of the system of FIG. 1, and is employed for receiving a sample whose refractive index or refractive index related characteristic properties are to be determined.

FIG. 2 shows a top view of the chip 20 showing the channel 22. An injection port 30 and an exit port 32 are laser drilled at opposite ends of the channel 22 to allow for introduction and removal of a fluid sample to be analyzed.

The laser beam 14 is directed to impinge upon the channel 22 at a point 34 that is a short distance (e.g., about 2 mm) from the exit port 32 and is graphically shown by the circle, labeled "detection zone", in FIG. 2.

Figure 3A:
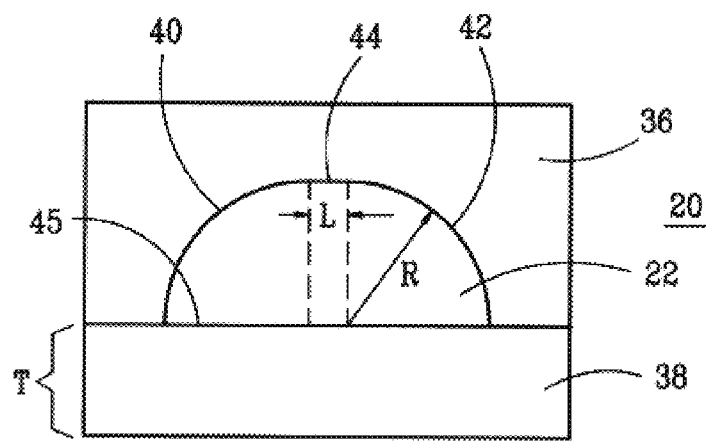
FIGS. 3A and 3B are sectional views of the chip of FIG. 2 showing the shape of the channel, with FIG. 3A being taken along line 1—1 of FIG. 2, and FIG. 3B being taken along line 2—2 of FIG. 2.
Figure 3B:
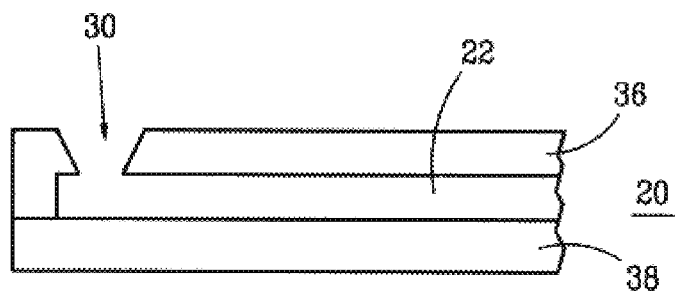

As illustrated in FIGS. 3A and 3B, the chip 20 preferably consists of first and second substrate pieces 36 and 38 that are fused together, with the channel 22 being formed in the first, top substrate piece 36, and having a generally hemispherical cross-sectional shape. The hemisphere has a radius R of between 5 and 150 microns, and most preferably between 10 and 50 microns. Although it is prefererred that the channel 22 be truly hemispherical in shape, to accommodate conventional etching techniques, the channel 22 is formed by first etching a first 90 degree arc 40 in the top substrate piece 36, and then etching a second 90 degree arc 42. This etching process inherently results in the formation of a short, flat portion or segment 44 between the first and second arcs 40 and 42. The length L of the flat portion 44 should be as short as possible, preferably 5–25 microns. Surprisingly, as long as the length of the flat portion 44 does not exceed the length of the channel radius R, there is no adverse effect on the interference fringes that are generated by the channel 22. The second, bottom substrate piece 38 forms a floor 45 of the channel 22, and has a thickness T that is approximately one third to one times the radius R of the arcs 40 and 42.

Interestingly, even though the channel 22 is of the general shape of a hemisphere or half circle, including the flat portion 44, relatively high contrast interference fringes (much like those seen with full capillaries) have been observed in experiments on a prototype of the invention. The inherent characteristics of the channel 22 result in a multi pass optical configuration in which multi path reflections occur, and increase the sensitivity of the detector system 10. A typical interference pattern produced by an unmodified chip filled with distilled/deionized water is shown in the false color intensity profile (black no photons and white is the intensity for detector saturation) shown in FIG. 4. These observations are very exciting because, 1) the features (arcs 40 and 42) on the chip 20 that produce the interference fringes are quite common and easy to manufacture, 2) no additional optics are needed, and 3) the fringes have very high contrast allowing sensitive detection of optical pathlength changes. It is noteworthy that all of the measurements are obtained using a very simple optical train with no additional focusing or collection optics and using a chip that has no reflective coatings. In short, the chip-scale RI detector configuration uses unaltered chips.

Numerous experiments have been conducted to verify the operation of the on-chip detection system 10, and determine which components provide the best sensitivity. A first experiment using varying concentrations of a glycerol solution was performed to evaluate the detection system 10 using the CCD camera and the laser beam analyzer for measuring fringe movement. The fringe movement varies linearly with concentration (change in RI) over 2 decades. The limit of detection calculated at 3σ was 31.47 mM of solute and was limited mainly by the LBA software.

In a second experiment, to improve the sensitivity of the on-chip RI measurement, the neutral density filters 16 were removed and a slit/photodetector assembly was used instead of the CCD camera/laser beam analyzer system. In this experiment, the slit/photodetector assembly was located on the order of 28 cm from the front surface of the chip 20. The photodetector 25 consisted of a pin photodiode integrated with a 632.8 nm interference filter (Coherent-Ealing) wired with a simple current to voltage circuit. A 50-micron precision air slit (Melles Griot) was mounted vertically in the center of the active surface area of the photodiode. The voltage output from the photodiode was then amplified (Gain=100) by a low-noise preamplifier (Stanford Research Systems) using a 30 Hz low pass filter (12 dB/octave). The analog signal from the preamplifier was then digitized with an external DAQ board (PPIO-AIO8, CyberResearch, Branford, Conn.) and displayed on the PC computer 28 running a digital strip-chart recorder (Labtech for Windows).

The slit-photodetector assembly was aligned on the edge of a fringe in order to monitor fringe movement. The position of the assembly corresponds to the edge of the sloping intensity gradient of the working fringe and is located at $I=1/e^2$ of the intensity distribution. Since the intensity of a backscattered fringe is essentially Gaussian, a change in refractive index of the solution in the probe volume produces a change in the light intensity striking the active surface of the photodetector 25. As the fringe shifts, a small voltage output from the photodetector 25 is observed, which is linearly proportional to a change in refractive index ($\Delta n$).

A calibration curve was generated with the slit/photodetector using the exact same procedure and glycerol solutions of the same concentrations as with the CCD/LBA configuration. The $3\sigma$ detection limit for the backscatter detector using a slit/photodetector assembly was found to be 18.33 mM, substantially better than the 31.47 mM limit achieved with the CCD/LBA experimental set up. The lower detection limits are achievable with a slit/photodetector assembly since small positional shifts of the backscattered fringes result in large intensity changes due to their pseudo-Gaussian intensity profile. The CCD/laser beam analyzer system measures only positional shifts, which are considerably less sensitive than the intensity changes seen by the slit/photodetector assembly.

In a third experiment, to improve the S/N of the measurement still further, the photodetector 25 was a small area avalanche photodiode (e.g., such as those available from Texas Optoelectronics, Inc.). The avalanche photodiode (APD) was operated near the breakdown voltage and driven with a reverse bias. The APD was aligned on the edge of the fringe as described for the slit/photodetector assembly, and fringe movement was denoted by changes in intensity. The signal from the APD was digitized with an external DAQ board (PPIO-AIO8, CyberResearch, Branford, Conn.) and displayed on the PC computer 28 running a digital stripchart recorder (Labtech for Windows).

Running tests on a series of glycerol solutions, revealed that the $3\sigma$ detection limit for glycerol is just 4.1 mM. By using the APD (even at a wavelength, 632.8 nm, where the device has poor quantum efficiency) a 4.4 fold S/N gain is realized.

Still further increases in sensitivity have been realized in subsequent experiments using a bi-cell position photodetector, and a diode laser with special optics to produce a pseudo-Gaussian beam of approximately 75 $\mu$m, at a distance of 50 cm and over a relatively long focal length. In this study the detection volume was 188 picoliters and a $2\sigma$ concentration detection limit for glycerol of 494 $\mu$M ($139 \times 10^{-15}$ moles or 12.8 picograms of solute) was attained, without active thermal control. Thus, a reduction in the volume and an increase in sensitivity were realized as a consequence of several technical modifications to the system.

The detection limits achieved in the foregoing experiments represent the lowest RI detection limits that have been achieved to date with a system that is compatible with chip-scale sensing (low nanoliter detection volumes). For reference, MIBD is already an order of magnitude more sensitive than the holographic forward scatter technique.

A few important points should be made at this juncture. First, the detection limits were accomplished without any active thermal control of the chip (resulting in increased noise due to thermal perturbations in the dc mode (i.e. no wavelength modulation)) and using minimal active electronic filtering. In measurements of refractive index (n), the primary source of noise is thermal sensitivity. For most cases involving fluids, n has a relatively high thermal coefficient (dn/dT), requiring very precise temperature stabilization of the system. As an example, dn/dT for $H_2O$ is on the order of $8 \times 10^{-4\circ}$ C., so at an analytically useful detection limit for $\Delta n$ of one part in $10^6$, the temperature-induced signal corresponds to a change in T of $1 \times 10^{-2\circ}$ C. Therefore, thermal stability of the system must be maintained at the millidegree centigrade label, to determine n to one part in $10^8$. This level of temperature control can be achieved using a thermostated flow cell with active control using a Peltier thermoelectric cooling chip (e.g., such as is available from Melcore, Trenton, N.J.) controlled by a power supply (e.g., ILX Lightwave, Bozeman, Mont.) wired in feedback from a calibrated thermocouple.

Conversely, as discussed previously, the thermal "noise" in RI measurements can be used to the advantage of the analyst. For example, thermal sensitivity can be used to determine minute temperature changes in small-volume following streams, non-invasive process stream monitoring, and even protein folding. The relationship between dn and dT is linear. Therefore, MIBD can be used to measure thermal changes at a microdegree centigrade level and to determine dn/dT for fluids.

To demonstrate use of the system 10 of FIG. 1 for detecting temperature changes, another experiment was conducted. In this experiment, thermometry was performed in a probe volume of just $3.14 \times 10^{-9}$ L as defined by the diameter of the laser beam 14 and the radius (in this case, 50 microns) of the etched channel 22. Distilled/deionized water was hydrodynamically injected into the channel 22 and allowed to temperature and pressure stabilize. Next the temperature of the channel 22 was manually changed in approximately 0.3° C. increments, the sample was allowed to temperature stabilize, and a relative change in refractive index measurement was obtained. Upon graphing the results of relative change in RI versus temperature for water, a detection limit of 0.011° C. (11 millidegree C.) was determined based on the 3 sigma statistics. These results confirm that the signal analyzer 28 can be programmed to determine the temperature of the sample from an analysis of the fringe pattern signals with a high degree of sensitivity.

Figure 5:
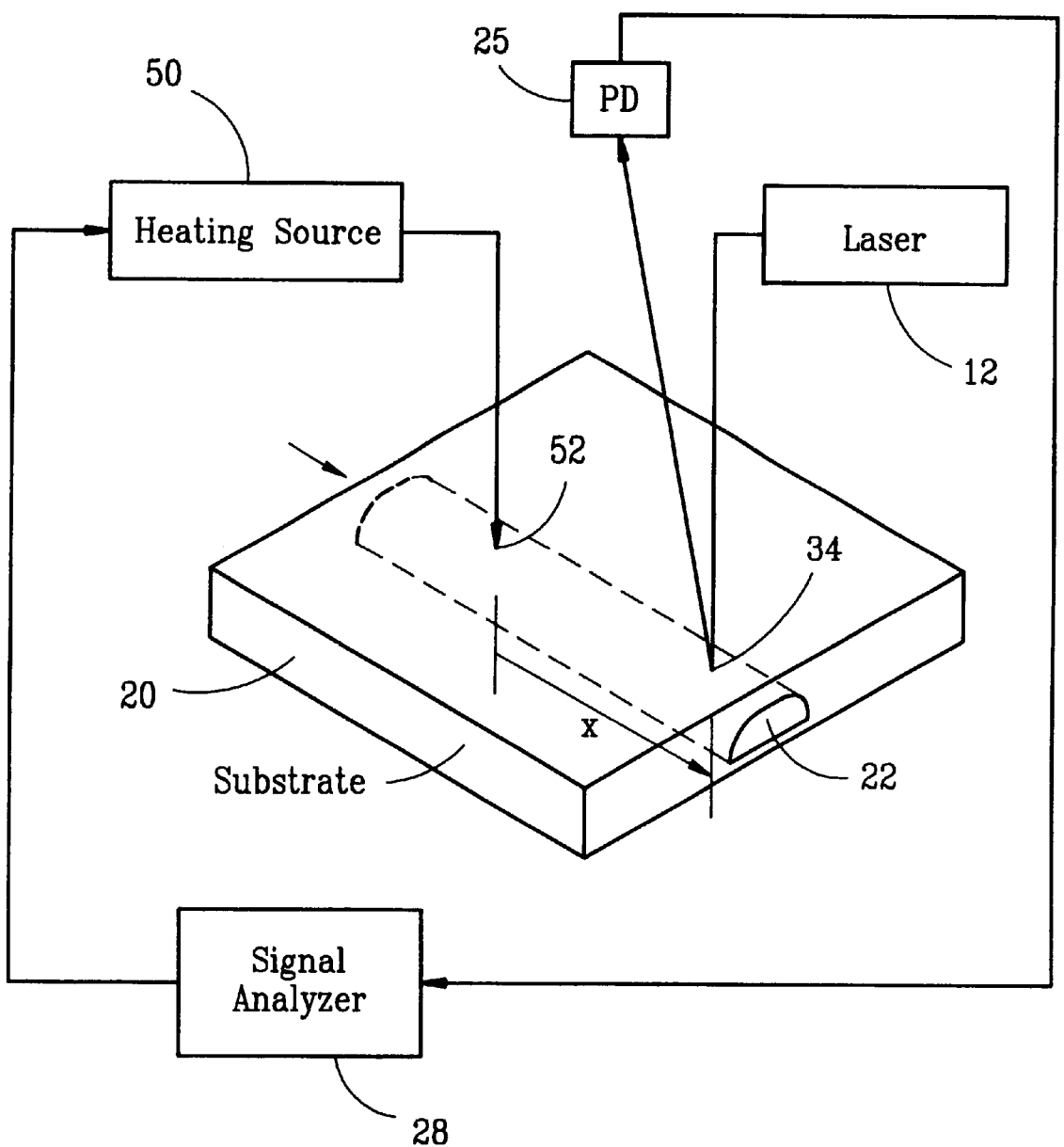
FIG. 5 is a schematic illustration of a second preferred embodiment of the present invention that is employed for measuring the flow rate of a flow stream.

Another embodiment of the present invention is illustrated in FIG. 5. This embodiment is designed for measuring the flow rate of a flow stream flowing through the channel 22. The signal analyzer 28 in this embodiment contains timing circuitry or programming, and controls operation of a heating source 50 that provides localized heating of a point 52 along the channel 22 that is spaced a known distance x from the detection zone 34. Preferably, the heating source is an infrared laser that can provide rapid localized heating of a sample flow stream in the channel 22.

In the operation of this embodiment, the heating source 50 is triggered at a first instant in time to provide the localized heating of a portion of the flow stream. This creates a temperature perturbation in the flow stream that moves toward the detection zone 34. The signal analyzer 28 then monitors the intensity signals generated by the photodetector 25, and detects therefrom, the instant in time when the temperature perturbation arrives at the detection zone 34. The time interval between when the flow stream was heated and when the temperature perturbation is detected is then employed with the value of x to determine the flow rate of the flow stream.

Figure 6:
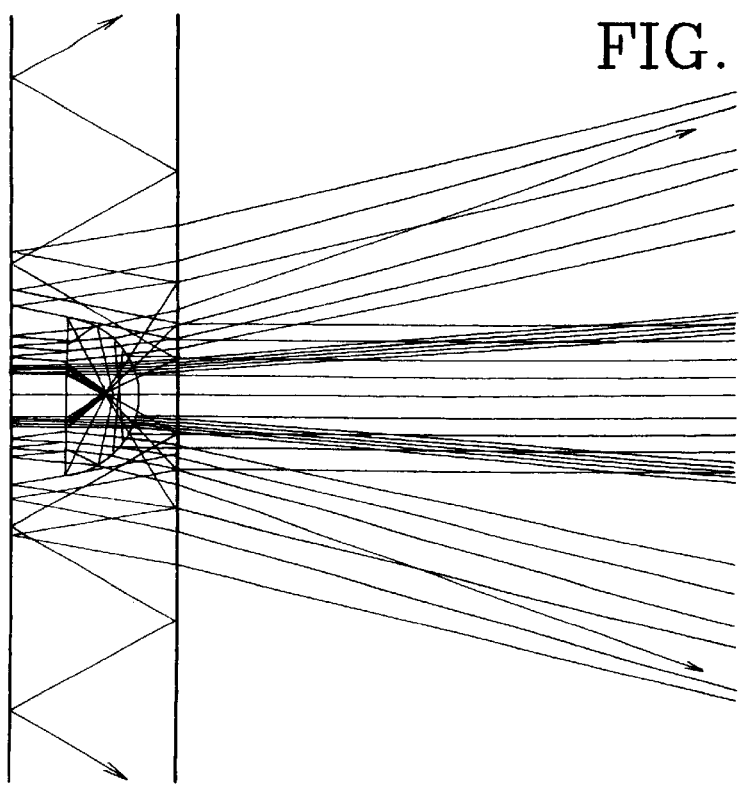
FIG. 6 is a schematic illustration of the interaction of an incident laser beam on the curved channel of the system of FIG. 1.

Using ASAP (an optical modeling program from Breault Research, Tuscon Ariz.) a few preliminary modeling experiments were performed to demonstrate the multi pass optical configuration provided by the channel 22, and the path length insensitivity that results. In the first investigation illumination impinges onto the etched side of the chip 20, so that the light impinges on the curved surface just after entering the substrate. FIG. 6 illustrates the results of this simulation, and clearly shows the multipath reflections that increase the system's sensitivity, or leads to an inherent insensitivity of performance on the size of the channel 22. Put another way, the multi pass configuration eliminates optical path length constraints, thus allowing for smaller and smaller detection volumes. In FIG. 6, 9 initial rays are traced through a chip with an etched channel with a diameter of 100 $\mu$m. The laser source is located at some distance in +Z direction. Splits (the number of rays that will continue at interfaces) are set to 3. The middle plane simulates the lid that covers the channel. Since the index refraction on both sides of that plane is the same its presence does not affect the rays intersecting that plane. Since the rays that continue to travel in the −Z direction, after they passed through the chip, do not contribute to the formation of the backscattered fringe pattern they are ignored and dropped out of simulation.

It is certain that even lower detection limits for MIBD are possible. First, simply increasing the distance of the photodetector 25 from the front surface of the etched channel 22 will produce larger "apparent" fringe movement because angular displacement grows as the detector to channel distance increases. In general, this geometric relationship dictates sensitivity to angular displacement and indicates that every 2 fold increase in distance will produce at least a 2 fold sensitivity improvement. Second, lower detection limits will be achieved by using either a longer wavelength laser or an APD whose sensitivity is maximized at the wavelength of the laser used. For example, at the He/Ne wavelength of 632.8 nm, the radiant responsivity of the current detector is approximately 10 A/W, but at the wavelength of 700 nm, the radiant responsivity of the device increases by a factor of three to 30 A/W. As a result, detection limits are predicted to improve by at least 3-fold. Third and finally, the detection volume for MIBD on a chip can be further reduced by using a smaller diameter laser beam (e.g., lasers generating 10 $\mu$m diameter beams are available), or a fiber couple diode laser combined with a smaller radius channel.

A few observations should be made at this point concerning the type of laser employed in the detector system 10. While HeNe lasers have excellent optical properties, they are limited in applications that demand miniaturization by their bulky size. As a result, VCSELs and diode lasers are replacing HeNe lasers in many industrial, medical, and analytical applications. VCSELs and diode lasers, in general, are solid state, low-cost compact, light sources that possess many of the properties of gas lasers (HeNe's). Among them are good beam quality (TEM$_{00}$), low divergence, and some polarization purity. Furthermore, they have characteristic long lifetimes (in excess of 50,000 hours), and provide reasonable coherent lengths (as great as 1 meter). VCSELs and diode lasers differ, however, from HeNe lasers in several important ways, particularly when using them as interferometry sources. First, wavelength stability of most VCSELs and diode lasers is generally poor due the device's structure (small cavity size), resulting in a dependency on and sensitivity to current and temperature changes. Second, while emitting light that is inherently linearly polarized, the polarity purity of a VCSEL's or diode laser's beam is relatively low (100:1). Nevertheless, if proper care is taken, VCSELs and diode lasers are low cost, coherent light sources that are adequate for interferometric detection schemes such as MIBD for both RI and polarimetric detection.

Figure 7:
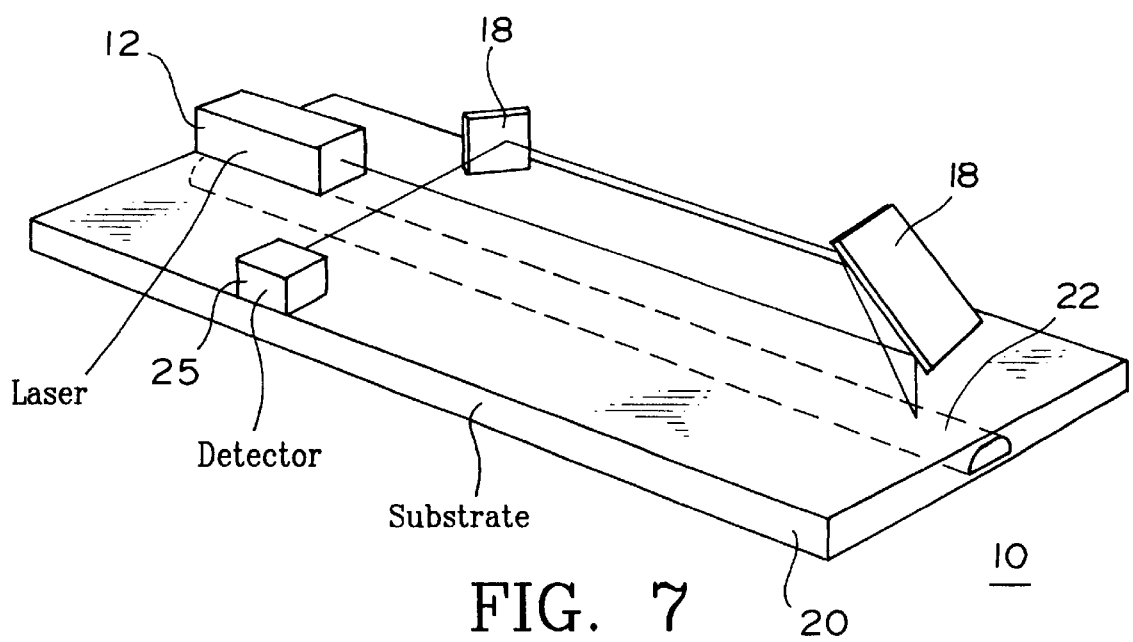
FIG. 7 is a schematic block diagram of another embodiment of the invention in which all of the system elements are formed on a single microchip.

One of the most important advantages of VCSELs and diode lasers in the present application, is that they facilitate reduction in size of the RI detector system 10 to the point of being incorporated directly onto the chip 20. FIG. 7 illustrates such an embodiment in which both the laser 12 and the photodetector 25 are formed integrally with the chip 20.

Another advantage of using VCSELs or laser diodes in interferometry is that their optical output (wavelength) can be easily modulated through the supply current. Wavelength modulation opens a path to potential alternative detection schemes in on-chip RI detection using micro-interferometry as a method of decreasing the thermal sensitivity of the measurement and lowering the limit of detection of the technique. Thus, the system 10 can be configured so that detection is performed in the AC regime (source wavelength modulation).

When wavelength modulation techniques are used with VCSELs and diode lasers, it is possible to make exceeding sensitive optical absorbance measurements. In fact the sensitivity possible approaches the shot noise limit, i.e. $10^{-7}$ AU in a 1 Hz bandwidth. Furthermore, with the advent of rapidly tunable (over a wide wavelength range), single mode, circular beam VCSELS, these devices are suitable sources for the on-chip interferometric detection technique. In short, by using such an approach for on-chip RI detection based on micro-interferometry, a significant (as much as 500 fold) improvement in S/N may be achievable for the instrument.

In conclusion, using on-chip RI detection based on micro-interferometry, the present invention performs interference detection in channels with ultra-small volumes and with a simple optical configuration that requires no additional optics. The on-chip RI detector is an effective universal detection system that expands the ability to sense or detect otherwise invisible solutes, particularly those important to proteomic analysis and high throughput screening. The detector's S/N ratio is not hindered by volume reduction, its probe volume and detection volume are the same, it is a non-invasive method, and is universal in nature. Thus, the detector can potentially play an important role in integrated genomics technology. It should also allow protein folding and biochemical bonding measurements previously not possible. Reaction kinetics can be followed in nanoliter volumes, and millidegree temperature changes can be quantified. Finally, the invention allows the further development of $\mu$-TAS and other techniques for cellular level analysis.

Although the invention has been disclosed in terms of a number of preferred embodiments and variations thereon, it will be understood that numerous modifications and additional variations could be made thereto without departing from the scope of the invention as defined in the following claims.

What is claimed is:

1. An interferometric detection system comprising:

a) a substrate;

b) a channel formed in said substrate for reception of a liquid sample to be analyzed;

c) a coherent light source for generating a coherent light beam, said light source being positioned to direct said light beam onto said substrate such that said light beam is incident on said channel to thereby generate backscattered light through reflective and refractive interaction of said light beam with a substrate/channel interface and said sample, said backscattered light comprising interference fringe patterns including a plurality of spaced light bands whose positions shift in response to changes in the refractive index of said liquid sample;

d) a photodetector for receiving said backscattered light and generating one or more intensity signals that vary as a function of positional shifts of said light bands; and e) a signal analyzer for receiving said intensity signals, and determining therefrom, a characteristic property of said liquid sample in said channel.

2. The interferometric detection system of claim 1, wherein said substrate is formed from material selected from the group comprising silica and plastic, and said channel is etched therein.

3. The interferometric detection system of claim 2, wherein said channel has a generally hemispherical cross-sectional shape.

4. The interferometric detection system of claim 3, wherein said channel has an inner radius of no more than 150 microns.

5. The interferometric detection system of claim 4, wherein said channel has a radius of 10–50 microns.

6. The interferometric detection system of claim 3, wherein said channel includes first and second curved portions, each said curved portion defining a 90 degree arc, and a first flat portion connecting said first and second curved portions.

7. The interferometric detection system of claim 6, wherein said channel is further defined by a second flat substrate positioned on top of said first substrate.

8. The interferometric detection system of claim 6, wherein said channel has an inner radius of no more than 150 microns, and said flat portion connecting said first and second curved portions has a length no greater than said radius.

9. The interferometric detection system of claim 1, wherein said coherent light source is selected from the group comprising a VCSEL, an He/Ne laser and a laser diode.

10. The interferometric detection system of claim 9, wherein said coherent light source of is formed integrally on said substrate.

11. The interferometric detection system of claim 9, wherein said coherent light source of is a wavelength modulated laser.

12. The interferometric detection system of claim 9, wherein said photodetector is selected from the group comprising a CCD photodetector, a bi-cell position sensor and a photodiode.

13. The interferometric detection system of claim 12, wherein said photodetector is formed integrally on said substrate.

14. The interferometric detection system of claim 1, wherein said photodetector is selected from the group comprising a CCD photodetector, a bi-cell position sensor and a photodiode.

15. The interferometric detection system of claim 14, wherein said photodetector is formed integrally on said substrate.

16. The interferometric detection system of claim 1, wherein said signal analyzer includes means for determining temperature changes in said sample from said intensity signals.

17. The interferometric detection system of claim 16, wherein said signal analyzer comprises a computer programmed to determine temperature changes in said sample from said intensity signals.

18. The interferometric detection system of claim 1, wherein said signal analyzer includes means for determining the index of refraction of said sample from said intensity signals.

19. The interferometric detection system of claim 18, wherein said signal analyzer comprises a computer programmed to determine the index of refraction of said sample from said intensity signals.

20. The interferometric detection system of claim 1, further comprising means for heating a portion of said sample at a known time and at a point along said channel that is a known distance upstream from a detection zone at which said coherent light beam is directed into said channel, and said signal analyzer further includes:

1) means for monitoring said intensity signals to identify changes therein that are a result of the arrival of said heated portion of said sample at said detection zone; and 2) means for determining the flow rate of said sample from a time interval between when said portion of said sample is heated and said heated portion is detected in said detection zone using said intensity signals.

21. The interferometric detection system of claim 20, wherein said means for heating said portion of said sample comprises a laser.

22. The interferometric detection system of claim 20, wherein said signal analyzer comprises a computer that is programmed to determine the flow rate of said sample from said time interval between when said portion of said sample is heated and said heated portion is detected in said detection zone using said intensity signals.

23. A interferometric detection system comprising:

a) a silica substrate;

b) an etched channel formed in said substrate for reception of a liquid sample, said channel having a generally hemispherical cross sectional shape;

c) a laser source for generating a laser beam, said laser source being positioned to direct said laser beam into said channel to thereby generate backscattered light comprising interference fringe patterns, said fringe patterns including a plurality of spaced light bands whose positions shift in response to changes in the refractive index of said liquid sample;

d) a photodetector for receiving said interference fringe patterns and generating intensity signals corresponding thereto; and e) a signal analyzer for receiving said intensity signals, and determining therefrom, a characteristic property of said liquid sample in said channel.

24. The interferometric detection system of claim 23, wherein said channel includes first and second curved portions, each said curved portion defining a 90 degree arc, and a first flat portion connecting said first and second curved portions.

25. The interferometric detection system of claim 24, wherein said channel has an inner radius of no more than 150 microns, and said flat portion connecting said first and second curved portions has a length no greater than said radius.

26. The interferometric detection system of claim 24, wherein said channel is further defined by a second flat substrate positioned on top of said first substrate.

27. The interferometric detection system of claim 23, wherein said channel has an inner radius of no more than 150 microns.

28. The interferometric detection system of claim 23, wherein said laser is selected from the group comprising a VCSEL, an He/Ne laser and a laser diode.

29. The interferometric detection system of claim 28, wherein said laser is a wavelength modulated laser.

30. The interferometric detection system of claim 23, wherein said photodetector is selected from the group comprising a CCD photodetector, a bi-cell position sensor and a photodiode.

31. The interferometric detection system of claim 23, wherein said signal analyzer includes means for determining temperature changes in said sample from said intensity signals.

32. The interferometric detection system of claim 31, wherein said signal analyzer comprises a computer programmed to determine temperature changes in said sample from said intensity signals.

33. The interferometric detection system of claim 23, wherein said signal analyzer includes means for determining the index of refraction of said sample from said intensity signals.

34. The interferometric detection system of claim 33, wherein said signal analyzer comprises a computer programmed to determine the index of refraction of said sample from said intensity signals.

35. The interferometric detection system of claim 23, further comprising means for heating a portion of said sample at a known time and at a point along said channel that is a known distance upstream from a detection zone at which said coherent light beam is directed into said channel, and said signal analyzer further includes:

1) means for monitoring said intensity signals to identify changes therein that are a result of the arrival of said heated portion of said sample at said detection zone; and 2) means for determining the flow rate of said sample from a time interval between when said portion of said sample is heated and said heated portion is detected in said detection zone using said intensity signals.

36. The interferometric detection system of claim 35, wherein said means for heating said portion of said sample comprises a laser.

37. The interferometric detection system of claim 35, wherein said signal analyzer comprises a computer that is programmed to determine the flow rate of said sample from said time interval between when said portion of said sample is heated and said heated portion is detected in said detection zone using said intensity signals.

38. A method for determining a characteristic property of a liquid comprising the steps of:

a) providing a substrate having a channel formed therein for reception of a liquid sample to be analyzed;

b) injecting a liquid sample to be analyzed into said channel;

c) directing a coherent light beam onto said substrate such that said light beam is incident on said channel to generate backscattered light through reflective and refractive interaction of said light beam with a substrate/channel interface and said sample, said backscattered light comprising interference fringe patterns including a plurality of spaced light bands whose positions shift in response to changes in the refractive index of said liquid sample;

d) detecting positional shifts in said light bands; and e) determining said characteristic property of said sample from said positional shifts of said light bands in said interference patterns.

39. The method of claim 38, wherein said step of providing a substrate further comprises providing a substrate having a channel formed therein with a generally hemispherical cross sectional shape.

40. The method of claim 39, wherein said channel is formed with first and second curved portions, each said curved portion defining a 90 degree arc, and a first flat portion connecting said first and second curved portions.

41. The method of claim 38, wherein said step of directing a coherent light beam into said channel further comprises directing a coherent light beam from a laser formed integrally on said substrate.

42. The method of claim 41, wherein said step of detecting positional shifts of said light band comprises detecting said positional shifts with a photodetector formed integrally on said substrate.

43. The method of claim 38, wherein said characteristic property comprises the index of refraction of said sample.

44. The method of claim 38, wherein said characteristic property comprises the temperature of said sample.

45. The method of claim 38, wherein said characteristic property comprises the flow rate of said sample, and said method further comprises the steps of:

1) heating a portion of said sample at a known time and at a point along said channel that is a known distance upstream from a detection zone at which said coherent light beam is directed into said channel;

2) monitoring said interference fringe patterns to identify positional shifts in said light bands that are a result of the arrival of said heated portion of said sample at said detection zone; and 3) determining the flow rate of said sample from a time interval between when said portion of said sample is heated and said heated portion is detected in said detection zone.

46. The method of claim 45, wherein said step of heating said portion of said sample comprises heating said portion with a laser beam.

47. The method of claim 38, wherein said step of directing a coherent light beam into said channel further comprises directing a wavelength modulated coherent light beam into said channel.

* * * * *